(12) United States Patent
Sato et al.

(10) Patent No.: US 11,259,850 B2
(45) Date of Patent: Mar. 1, 2022

(54) FEMUR FIXATION APPARATUS

(71) Applicant: OMIC CORPORATION, Ritto (JP)

(72) Inventors: Toru Sato, Ritto (JP); Kouji Imoto, Ritto (JP); Minoru Ito, Ritto (JP)

(73) Assignee: OMIC CORPORATION, Ritto (JP)

( * ) Notice: Subject to any disclaimer, the term of this patent is extended or adjusted under 35 U.S.C. 154(b) by 400 days.

(21) Appl. No.: 16/494,987

(22) PCT Filed: Sep. 7, 2018

(86) PCT No.: PCT/JP2018/033144
§ 371 (c)(1),
(2) Date: Sep. 17, 2019

(87) PCT Pub. No.: WO2020/049709
PCT Pub. Date: Mar. 12, 2020

(65) Prior Publication Data
US 2020/0289177 A1 Sep. 17, 2020

(51) Int. Cl.
*A61B 17/74* (2006.01)
*A61B 17/00* (2006.01)

(52) U.S. Cl.
CPC .. *A61B 17/744* (2013.01); *A61B 2017/00477* (2013.01)

(58) Field of Classification Search
CPC ... A61B 17/744; A61B 17/72–17/7291; A61B 17/74–17/748; A61B 2017/00477
See application file for complete search history.

(56) References Cited

U.S. PATENT DOCUMENTS

| | | | |
|---|---|---|---|
| 2011/0196370 A1* | 8/2011 | Mikhail | A61B 17/72 606/62 |
| 2015/0157369 A1* | 6/2015 | Ehmke | A61B 17/7241 606/64 |
| 2018/0250042 A1* | 9/2018 | Sato | A61B 17/744 |

FOREIGN PATENT DOCUMENTS

| | | |
|---|---|---|
| JP | 2012-507355 A | 3/2012 |
| JP | 2014-064613 A | 4/2014 |
| JP | 2016-195746 A | 11/2016 |
| JP | 2016-539724 A | 12/2016 |

(Continued)

OTHER PUBLICATIONS

Nov. 27, 2018 International Search Report issued in International Patent Application No. PCT/JP2018/033144.

(Continued)

*Primary Examiner* — Pedro Philogene
(74) *Attorney, Agent, or Firm* — Oliff PLC

(57) ABSTRACT

A femur fixation apparatus capable of firmly fixing in place an anti-rotation member, which includes an intramedullary nail, an anti-rotation pin configured to be inserted through the intramedullary nail, and an adjuster fitted in the intramedullary nail. The adjuster includes a rotation part and a sliding part. The rotation part is rotatably and threadedly engaged in the intramedullary nail and rotatably connected to the upper end of the sliding part. The sliding part is formed with a space through which the anti-rotation pin is inserted. An urging member extends from a side wall of the space into the space. When the rotation part is rotated in a predetermined direction relative to the intramedullary nail, then the adjuster moves downward, and the urging member presses downward and fixes in place the anti-rotation pin.

9 Claims, 13 Drawing Sheets

(56) References Cited

FOREIGN PATENT DOCUMENTS

| | | |
|---|---|---|
| JP | 2018-033616 A | 3/2018 |
| JP | 6293980 B1 | 3/2018 |

OTHER PUBLICATIONS

Nov. 27, 2018 Written Opinion of the International Searching Authority issued in International Patent Application No. PCT/JP2018/033144.

* cited by examiner

FEMUR FIXATION APPARATUS

TECHNICAL FIELD

The present invention relates to femur fixation apparatuses.

BACKGROUND

Bone fixation treatments using bone fixation apparatuses are widely performed for proximal femur fractures or femoral trochanter fractures. Because reduction at an early stage in bone fixation treatment and fixation methods have a huge effect on postoperative process, bone fixation apparatuses with a firm fixing force are needed for maintaining reduced positions. For better treatments, it is preferable that the number of anti-rotation members to use and insertion angles thereof be chosen according to conditions of bone fracture.

In this regard, a femur fixation apparatus disclosed in Patent Document 1 includes an intramedullary nail to be inserted into a femoral shaft, a lag screw and three anti-rotation pins to be inserted through the intramedullary nail, and a set screw (adjuster) installed in the intramedullary nail. Among the three anti-rotation pins, one anti-rotation pin is inserted through the intramedullary nail so as to be parallel with the lag screw, and the remaining two anti-rotation pins are inserted through the intramedullary nail such that they are oblique to the lag screw and that tip end sections of the anti-rotation pins intersect each other in a plan view. That is, the set screw having a sliding part with a relatively long length widens the choice of the number of the anti-rotation pins to use and the choice of insertion angles thereof, enabling excellent osteosynthesis.

In the configuration of Patent Document 1, however, because the anti-rotation pins are not fixed to the intramedullary nail, there is a danger that the anti-rotation pins loosen and come off (back out).

On the other hand, there have been proposed femur fixation apparatuses with urging members or resilient members for fixing lag screws or anti-rotation pins in place. For example, in a femur fixation apparatus disclosed in Patent Document 2, a second element of a rock mechanism which uses urging force of a coil spring is engaged with an abutting configuration of an implant (lag screw) to prevent inward movement of the lag screw.

Intramedullary fixation systems disclosed in Patent Documents 3 and 4 include an intramedullary nail body, a first engaging member accommodated in the intramedullary nail body, a second engaging member accommodated in the first engaging member, and a bone screw (an anti-rotation pin) to be inserted through the intramedullary nail body and the first engaging member. In these systems, a coil-shaped elastic member fitted around the second engaging member holds the second engaging member in an initial position. When an end cap is inserted into the intramedullary nail body, a distal end thereof presses down the second engaging member to hold the bone screw, thereby preventing the bone screw from coming off the intramedullary nail body.

A bone fixing system disclosed in Patent Document 5 includes an intramedullary nail body, an insert accommodated in the intramedullary nail body, and a plurality of bone screws to be inserted through the intramedullary nail body and the insert. The insert is formed with a plurality of openings arranged along an axis line, and each bone screw is inserted through the corresponding opening. When an end cap is screwed into the intramedullary nail body, the end cap presses down the insert toward a distal end, and each bone screw is pressed by a corresponding pair of elastic engaging parts toward the distal end and sandwiched in a transverse direction perpendicular to an axis direction of the intramedullary nail body. As a result, the bone screw is fixed to the intramedullary nail body.

RELATED ART

Patent Documents

Patent Document 1: Japanese Patent No. 6293980
Patent Document 2: Japanese Patent Application Publication No. 2012-507355
Patent Document 3: Japanese Patent Application Publication No. 2014-64613
Patent Document 4: Japanese Patent Application Publication No. 2016-195746
Patent Document 5: Japanese Patent Application Publication No. 2018-33616

SUMMARY

Problems to be Solved by Invention

Patent Document 2 discloses a configuration to fix in place the lag screw with the urging force of the coil spring. If the same lock mechanism as that of Patent Document 2 is employed for fixing in place a lag screw having no abutting configuration, however, there is a problem that fixing force is insufficient.

Because the configurations of Patent Documents 3 and 4 require the coil spring fitted around the first engaging member, the coil-shaped elastic member fitted around the second engaging member, and a deformable area defined by the slit formed in the second engaging member, there is a problem that the first engaging member has only a limited area where the bone screw can be inserted. Also, in the system of Patent Document 5, because the bone screw is sandwiched by the pair of elastic engaging parts in the transverse direction, in order to make a plurality of bone screws insertable in an alignment with one another in the transverse direction through the intramedullary nail body, the bone screws need to be thinner, making the bone screws weak and easy to break.

It is an object of the invention to provide a femur fixation apparatus that firmly fixes an anti-rotation member in place.

Means to Solve the Problems

A femur fixation apparatus according to one aspect of the invention includes: an intramedullary nail extending in a first direction; a first anti-rotation member configured to be inserted through the intramedullary nail; and an adjuster fitted in the intramedullary nail, wherein: the adjuster includes a rotation part and a sliding part extending in the first direction; the sliding part is unrotatable and slide-movable in the first direction relative to the intramedullary nail and has a first end on a first side in the first direction and a second end on a second side opposite to the first side in the first direction; the rotation part is rotatably and threadedly engaged in the intramedullary nail and rotatably connected to the first end of the sliding part; the sliding part is formed with a first space through which the first anti-rotation member is inserted; the sliding part has a first urging member extending from a side wall of the first space into the first space; and when the rotation part is rotated in a predetermined direction relative to the intramedullary nail, then the adjuster moves toward the second side relative to the intramedullary nail, and the first urging member presses toward the second side and fixes in place the first anti-rotation member.

A femur fixation apparatus according to another aspect of the invention includes: an intramedullary nail extending in a first direction; a lag screw configured to be inserted through the intramedullary nail; an anti-rotation member configured to be inserted through the intramedullary nail; and an adjuster fitted in the intramedullary nail, wherein: the adjuster includes a rotation part and a sliding part extending in the first direction; the sliding part is unrotatable and slide-movable in the first direction relative to the intramedullary nail and has a first end on a first side in the first direction and a second end on a second side opposite to the first side in the first direction; the rotation part is rotatably and threadedly engaged in the intramedullary nail and rotatably connected to the first end of the sliding part; the sliding part has a support part and a movable part movable in the first direction relative to the support part; the movable part has a main part and a spring part, the main part having a first end on the first side and a second end on the second side, the spring part extending from the second end of the main part toward the second side, the spring part being deformable in the first direction; the support part and the main part of the movable part are respectively formed with a first space and a second space through which the anti-rotation member is inserted; and when the movable part is pressed toward the second side, then the spring part is compressed, and the main part moves relative to the support part toward the second side, thereby fixing in place the anti-rotation member inserted through the first space and the second space.

Effects of the Invention

According to the femur fixation apparatus of one aspect of the invention, the sliding part has the first urging member extending from the side wall of the first space into the first space, and the first urging member presses, from the first side toward the second side, the first anti-rotation member inserted through the intramedullary nail and passing through the adjuster. Thus, it is possible to prevent the first anti-rotation member from coming out the intramedullary nail.

According to the femur fixation apparatus in the another aspect of the invention, when the movable part of the sliding part is pressed toward the second side, then the spring part is compressed, and the main part of the movable part moves relative to the support part toward the second side, thereby fixing the anti-rotation member in place. In this manner, it is possible to prevent the anti-rotation member from coming out the intramedullary nail.

DETAILED DESCRIPTION

First Embodiment

Figure 1:
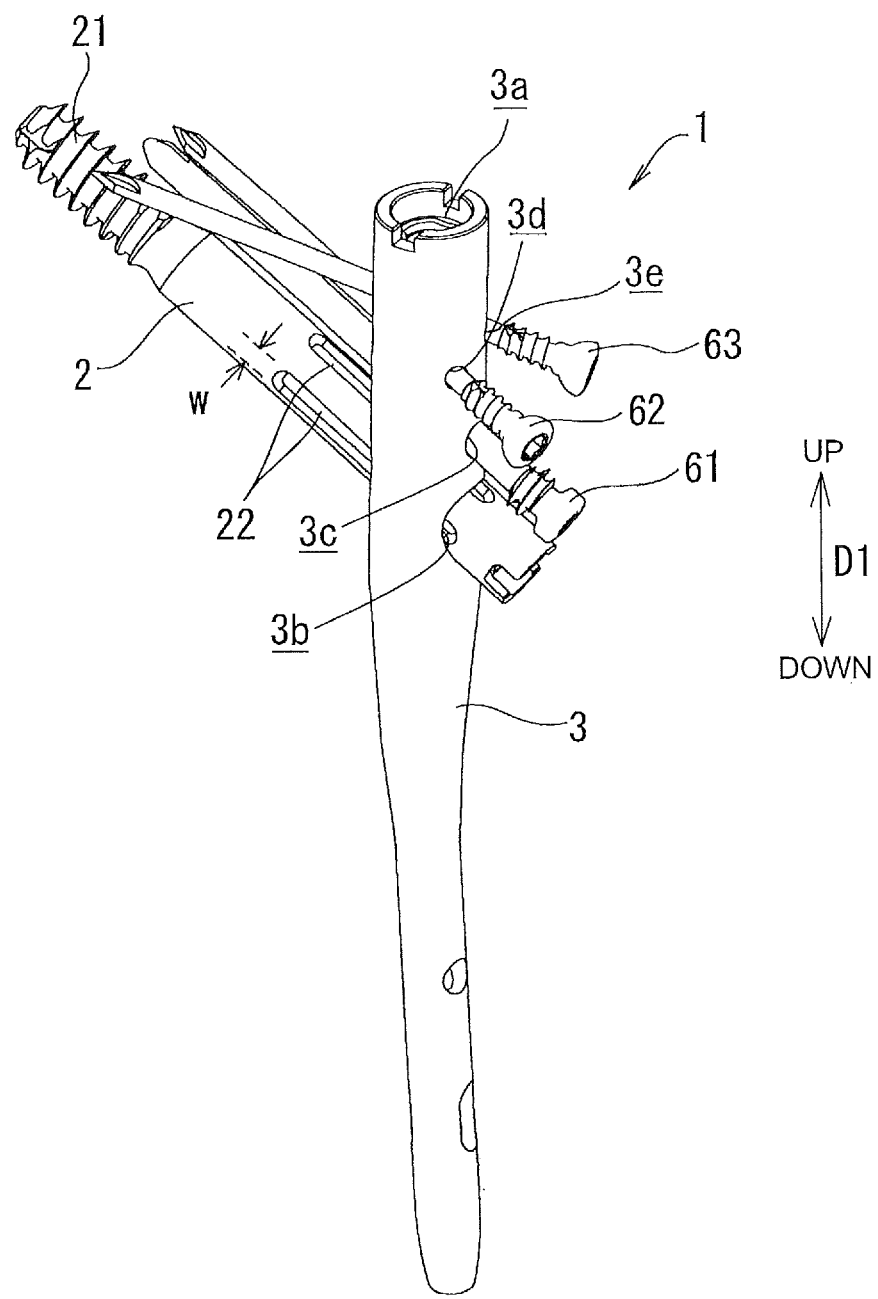
FIG. 1 A perspective view of a femur fixation apparatus according to a first embodiment of the invention FIG. 2 A partial cross-sectional view of the femur fixation apparatus of FIG. 1
Figure 2:
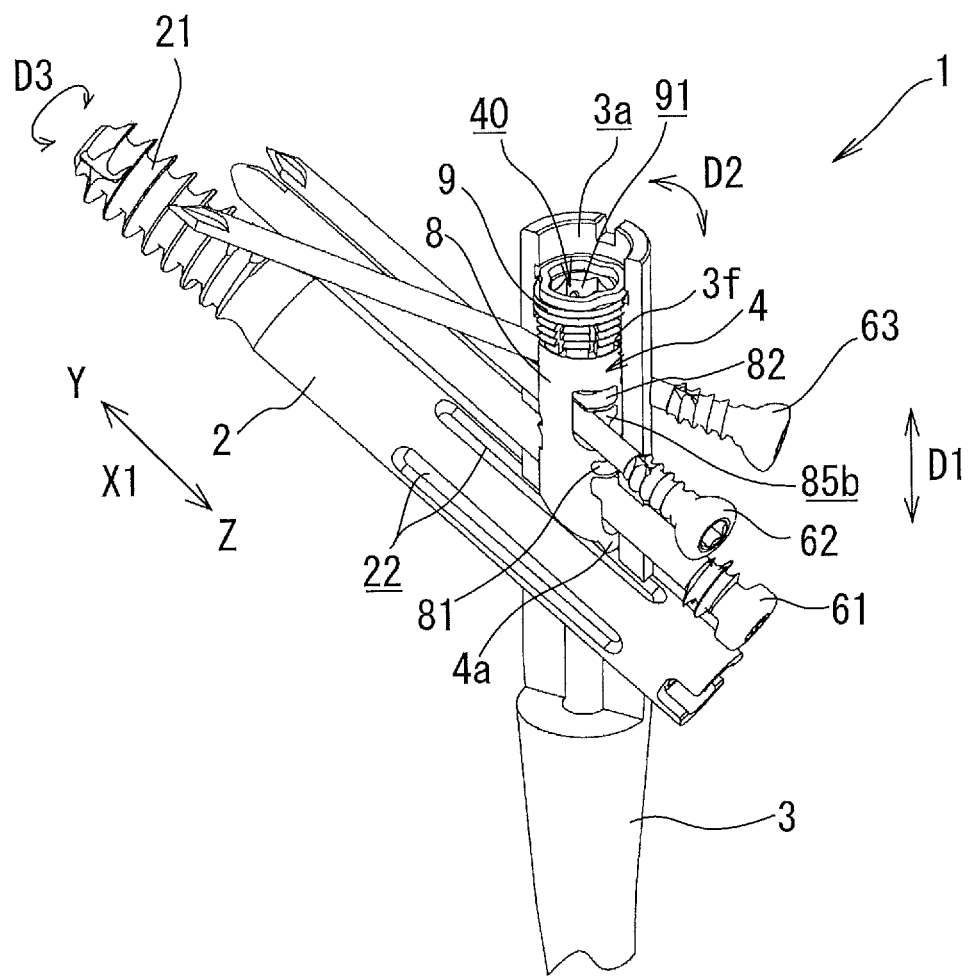
Figure 3:
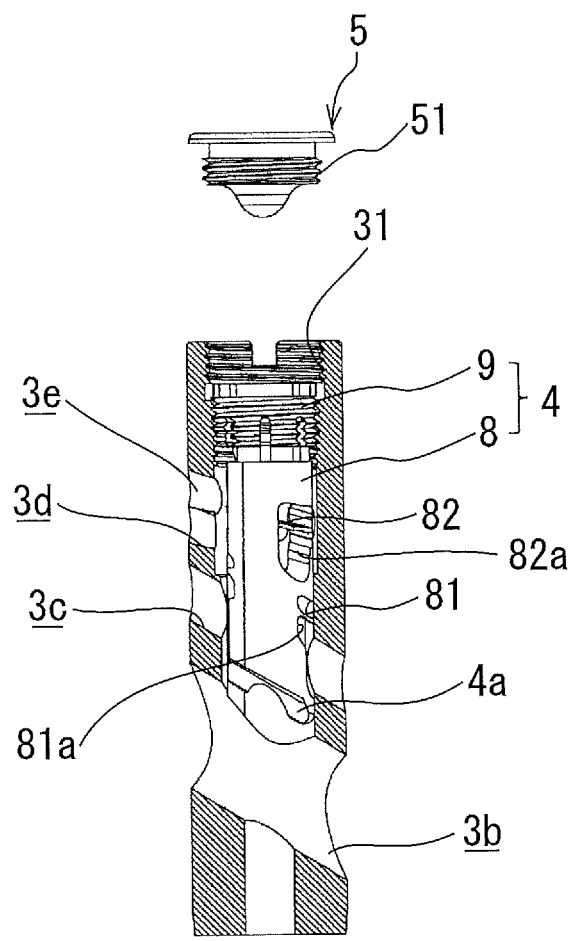
FIG. 3 A cross-sectional view of significant parts of the femur fixation apparatus of FIG. 1

A femur fixation apparatus according to a first embodiment of the invention will be described while referring to the accompanying drawings. With reference to FIGS. 1 to 3, a femur fixation apparatus 1 according to the embodiment is for use when proximal femoral fractures occur, and includes a lag screw 2 to be inserted into a bone including a head of a fractured femur, an intramedullary nail 3 to be inserted into a femoral shaft, an adjuster (a set screw) 4 fitted in the intramedullary nail 3, an end cap (cover member) 5 to be threadedly fitted into an upper end of the intramedullary nail 3, and one or more anti-rotation pins (in this example, three anti-rotation pins (anti-rotation members) 61, 62, 63) to be inserted through the intramedullary nail 3. The end cap 5 is omitted in FIGS. 1 and 2.

In the following explanation, a great trochanter side is described as an upper side (first side), and a distal end side is described as a lower side (second side), assuming that the femur fixation apparatus 1 is placed in a femur in a predetermined manner.

The lag screw 2 has one end in an axial direction X1 formed with a male screw part 21 and the other end formed with a plurality of grooves 22 extending in the axial direction X1 of the lag screw 2 at intervals in a circumferential direction D3. The width dimension W of each groove 22 gradually increases toward the one end formed with the male screw part 21 and gradually decreases toward the inner side in the radial direction of the lag screw 2 (depth direction).

Figure 5:
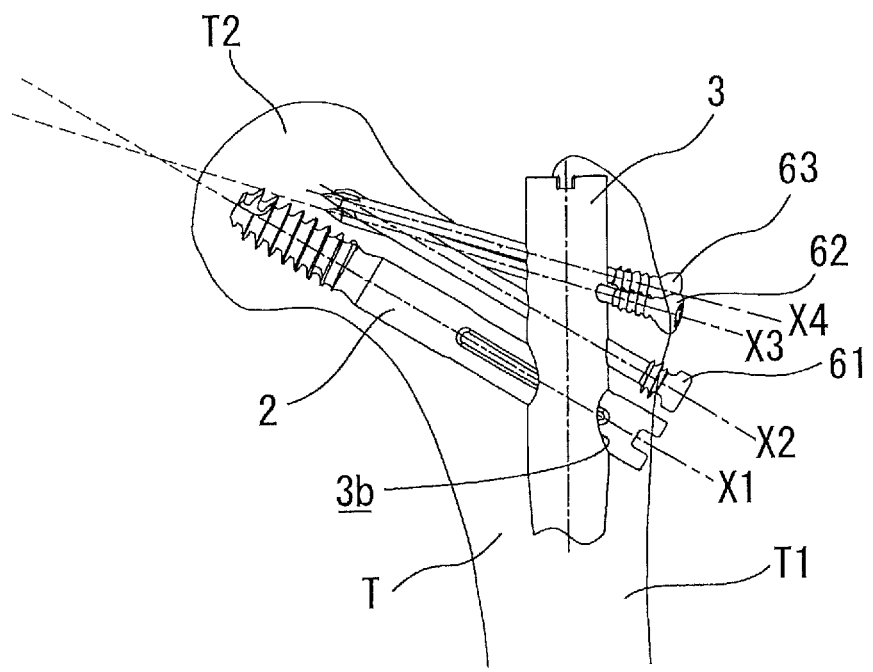

The intramedullary nail 3 extends in an up-down direction (first direction) D1 and is formed with a long hole 3$a$, a through hole 3$b$, and at least one auxiliary hole (in this embodiment, three auxiliary holes 3$c$, 3$d$, 3$e$). The long hole 3$a$ penetrates through the intramedullary nail 3 in the up-down direction D1 and is formed at an upper end of an inner surface thereof with a female screw part 31 that threadedly engages a male screw part 51 of the end cap 5 as shown in FIG. 3. The through hole 3$b$ and the auxiliary holes 3c to 3e are configured to be inserted with the lag screw 2 and the three anti-rotation pins 61 to 63, respectively, and are formed to penetrate through a peripheral surface of the intramedullary nail 3 and intersect the long hole 3a. As shown in FIG. 5, the length of the anti-rotation pins 61 to 63 is set such that their tip ends reach a femoral head T2 when they are inserted into a femur T in a predetermined manner.

As shown in FIG. 2, the adjuster 4 is fitted inside the long hole 3a of the intramedullary nail 3. The adjuster 4 is formed at its lower end with a stopper 4a. Engaging the stopper 4a with any one of the grooves 22 of the lag screw 2 prevents rotation of the lag screw 2 in the circumferential direction D3. Also, the adjuster 4 is formed with a through hole 40 that penetrates the adjuster 4 along the up-down direction D1.

Figure 4:
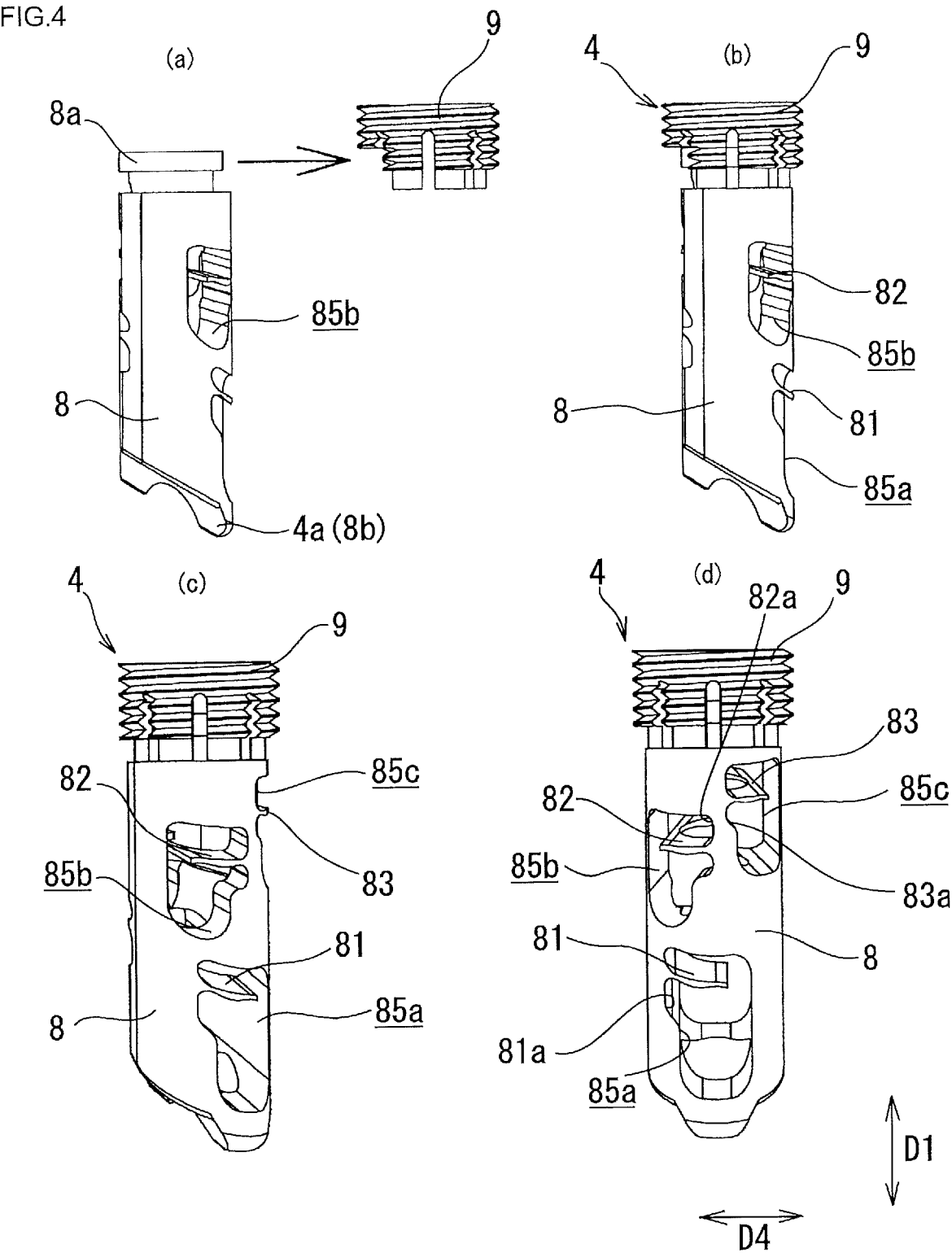
FIG. 4 Views of an adjuster of the femur fixation apparatus of FIG. 1, wherein (a) is an exploded view, (b) is a side view, (c) is a view as viewed from diagonally frontward, and (d) is a front view FIG. 5 A view showing the femur fixation apparatus of FIG. 1 used for a femur FIG. 6 A partial cross-sectional view of a femur fixation apparatus according to a second embodiment of the invention FIG. 7 A front view of an adjuster of the femur fixation apparatus of FIG. 6

The adjuster 4 includes a sliding part 8 and a rotation part 9. As shown in FIG. 4, the rotation part 9 is rotatably connected to an upper end 8a of the sliding part 8. The stopper 4a mentioned above is formed at a lower end 8b of the sliding part 8.

As shown in FIG. 2, the sliding part 8 is slidingly movable within the long hole 3a in the up-down direction D1, but is unrotatable with respect to the intramedullary nail 3 in a circumferential direction D2. Such a configuration is realized by, for example, the long hole 3a with a substantially D-shaped cross section and the corresponding sliding part 8 with a substantially D-shaped cross section.

The rotation part 9 is a male screw member with a threaded outer peripheral surface and threadedly engages with a female screw part 3f formed on an inner peripheral surface of the long hole 3a of the intramedullary nail 3. Also, the rotation part 9 is rotatable relative to the sliding part 8. When the rotation part 9 rotates relative to the intramedullary nail 3 in the circumferential direction D2, then the entire adjuster 4 moves in the up-down direction D1. At this time, the rotation part 9 moves up and down while rotating, but the sliding part 8 moves up and down without rotating relative to the intramedullary nail 3. Also, the rotation part 9 is formed at its upper part with an operation hole 91 which is a part of the above-mentioned through hole 40. The operation hole 91 is for insertion of an external operation tool (not shown). A hex wrench is used as the operation tool in this embodiment, and the operation hole 91 is formed to have a cross section in a hexagonal shape corresponding to a cross section of the hex wrench. Thus, an operator can rotate the rotation part 9 by inserting the hex wrench (not shown) into the operation hole 91 and rotating the same.

With reference to FIG. 4, the sliding part 8 is formed with a through hole (not shown) that penetrates through the sliding part 8 in the up-down direction D1 and that forms a part of the through hole 40, and is also formed with three interference prevention parts 85a, 85b, 85c corresponding to the auxiliary holes 3c to 3e. The interference prevention parts 85a to 85c are interference prevention holes and/or interference prevention grooves that extend in a direction intersecting the up-down direction D1. When inserted through the intramedullary nail 3, the anti-rotation pins 61 to 63 pass the interference prevention parts 85a to 85c, so interference with the sliding part 8 (the adjuster 4) is prevented.

More specifically, the interference prevention part 85a is a through hole the anti-rotation pin 61 penetrates through. The interference prevention part (first space) 85b is a space the anti-rotation pin (first anti-rotation member) 62 penetrates through, and is a through hole in this embodiment, and is located at a position higher than the interference prevention part 85a. The interference prevention part (second space) 85c is a space the anti-rotation pin (second anti-rotation member) 63 penetrates through, and is a through hole in this embodiment. The interference prevention part 85c is located at a position higher than the interference prevention part 85b and partially aligned with the interference prevention part 85b in a transverse direction (second direction) D4 perpendicular to the up-down direction D1.

The sliding part 8 also has an urging member 81 disposed in the interference prevention part 85a, an urging member (first urging member) 82 disposed in the interference prevention part 85b, and an urging member (second urging member) 83 disposed in the interference prevention part 85c. The urging member 81 is in a plate-like shape and extends from a sidewall 81a of the interference prevention part 85a in a direction intersecting the up-down direction D1 toward inside the interference prevention part 85a. The urging member 82 is in a plate-like shape and extends from a sidewall 82a of the interference prevention part 85b in a direction intersecting the up-down direction D1 toward inside the interference prevention part 85b. The urging member 83 is in a plate-like shape and extends from a sidewall 83a of the interference prevention part 85c in a direction intersecting the up-down direction D1 toward inside the interference prevention part 85c.

The femur fixation apparatus 1 with the above-described configuration is fitted to a femur in a manner described next. With reference to FIGS. 2 and 5, the intramedullary nail 3 with the adjuster 4 preset therein is inserted into marrow of the femoral shaft T1 to a predetermined depth from the above in the drawings. Next, the lag screw 2 is inserted through the through hole 3b of the intramedullary nail 3 into the femur T to a necessary depth toward the femoral head T2.

Next, the anti-rotation pins 61 to 63 are inserted through the auxiliary holes 3c to 3e (FIG. 1) of the intramedullary nail 3 into the femur T. At this time, the anti-rotation pins 61 to 63 are smoothly inserted without interfered with the adjuster 4 because the interference prevention parts 85a to 85c are formed in the adjuster 4. It should be noted that the anti-rotation pins 61 to 63 are inserted through parts of the interference prevention parts 85a, 85b, 85c below the urging members 81, 82, 83.

The anti-rotation pin 61 inserted in this manner is located above the lag screw 2, and an axial direction X2 of the anti-rotation pin 61 extends substantially parallel to the axial direction X1 of the lag screw 2. Also, the anti-rotation pins 62 and 63 are located above the anti-rotation pin 61. In a front view, the axial directions X3 and X4 of the anti-rotation pins 62 and 63 extend diagonal to the axial direction X1 of the lag screw 2 (and the anti-rotation pin 61). Also, in a plan view, the axial directions X3 and X4 of the anti-rotation pins 62 and 63 extend diagonal to each other such that tip ends of the anti-rotation pins 62 and 63 intersect each other in the transverse direction.

Because the anti-rotation pins 62 and 63 extending diagonal to the lag screw 2 in the up-down direction D1 can be used, it is possible to insert the anti-rotation pins 62 and 63 at an angle perpendicular or nearly perpendicular to a diagonally-extending fracture line, fixing the fractures more effectively.

In this state, the rotation part 9 of the adjuster 4 is rotated in a predetermined fastening direction with an external operation tool (not shown (a hex wrench, for example)) to lower the entire adjuster 4. When the adjuster 4 is lowered to a predetermined position, then the stopper 4a is engaged into the groove 22. As a result, the rotation of the lag screw 2 in the circumferential direction D3 is prevented. Also, the anti-rotation pins 61, 62, 63 are pressed downward by the urging members 81, 82, 83 and fixed, and thus the anti-rotation pins 61, 62, 63 are prevented from coming off the intramedullary nail 3. That is, the urging members 81 to 83 of the present embodiment function as leaf springs to press the anti-rotation pins 61 to 63.

More specifically, because the width dimension W of the grooves 22 gradually increases toward the one end of the lag screw 2 formed with the male screw part 21, the stopper 4a is allowed to slide-move within the groove 22 toward the one end in a direction indicated by an arrow Y but is prevented to move toward the other end in a direction indicated by an arrow Z. This means that the lag screw 2 is allowed to move in the direction of the arrow Z relative to the intramedullary nail 3 but is prevented from moving in the direction of the arrow Y relative thereto. In this manner, the lag screw 2 is prevented from accidentally moving in the direction of the arrow Y relative to the intramedullary nail 3 and projecting out from the femoral head T2. It should be noted that this state in which the lag screw 2 is prevented from moving in the direction of the arrow Y but is allowed to move in the direction of the arrow Z is referred to as a slidable state.

Also, when the adjuster 4 is lowered as described above, then the urging members 81 to 83 abut the anti-rotation pins 61 to 63, respectively, from above. When the adjuster 4 reaches the above-mentioned predetermined position, then the urging members 81 to 83 urge the anti-rotation pins 61 to 63 downward, and the anti-rotation pins 61 to 63 are sandwiched and fixed between the urging members 81 to 83 and bottom walls of the auxiliary holes 3c, 3d, 3e of the intramedullary nail 3 (or the femur T that the anti-rotation pins 61 to 63 are inserted into), so that the anti-rotation pins 61 to 63 are prevented from coming off the intramedullary nail 3.

When the rotation part 9 of the adjuster 4 in this condition is further rotated in the predetermined fastening direction, then the stopper 4a is further firmly pressed against the lag screw 2, preventing the lag screw 2 from moving relative to the intramedullary nail 3 in the direction of the arrow Z in addition to the direction of the arrow Y, and thus the lag screw 2 is completely fixed to the intramedullary nail 3. This state in which the relative movement of the lag screw 2 both in the direction of the arrow Y and in the direction of the arrow Z is referred to as a completely locked state. In this state also, the anti-rotation pins 61 to 63 are maintained pressed and fixed by the urging members 81 to 83.

As described above, in this embodiment, because the urging members 81 to 83 press the anti-rotation pins 61 to 63, the anti-rotation pins 61 to 63 are firmly fixed when the lag screw 2 is in either the slidable state or the completely fixed state. Also, because the urging members 81 to 83 press downward and fixes in place the anti-rotation pins 61 to 63, even in the configuration where the interference prevention part 85b and the interference prevention part 85c are partially aligned with each other in the transverse direction D4 as described above, it is unnecessary to excessively thin the diameter of the anti-rotation pin 61, 62 to be inserted therethrough, making it possible to maintain the strength of the rotation prevention pin 62, 63.

Because, unlike Patent Document 2, a space for accommodating a coil sprig is unnecessary, the length of the sliding part 8 of the adjuster 4 can be set long to secure a sufficient area through which the anti-rotation pin can be inserted. Also, unlike Patent Documents 3 and 4, it is unnecessary to fit a coil-shaped resilient member around the adjuster 4. For this reason also, the adjuster 4 can have a sufficient area through which the anti-rotation pin can be inserted.

It should be noted that the operator does not necessarily use all of the anti-rotation pins 61 to 63, but may use any one or more of them depending on the fracture type and condition or use none of them.

Also, in this embodiment, the interference prevention parts 85a, 85b, 85c are formed with the urging members 81 to 83, respectively. In a different embodiment, however, it is preferable that one or two of the urging members 81 to 83 be dispensed with.

Second Embodiment

Figure 6:
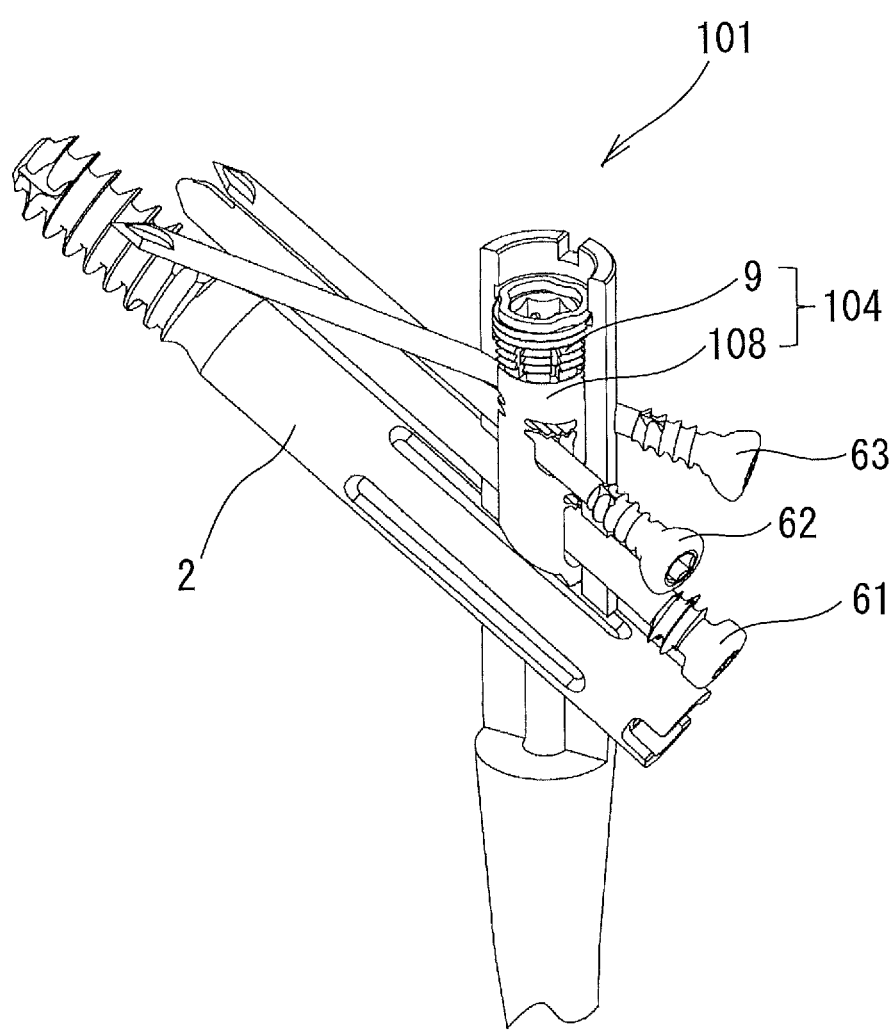
Figure 7:
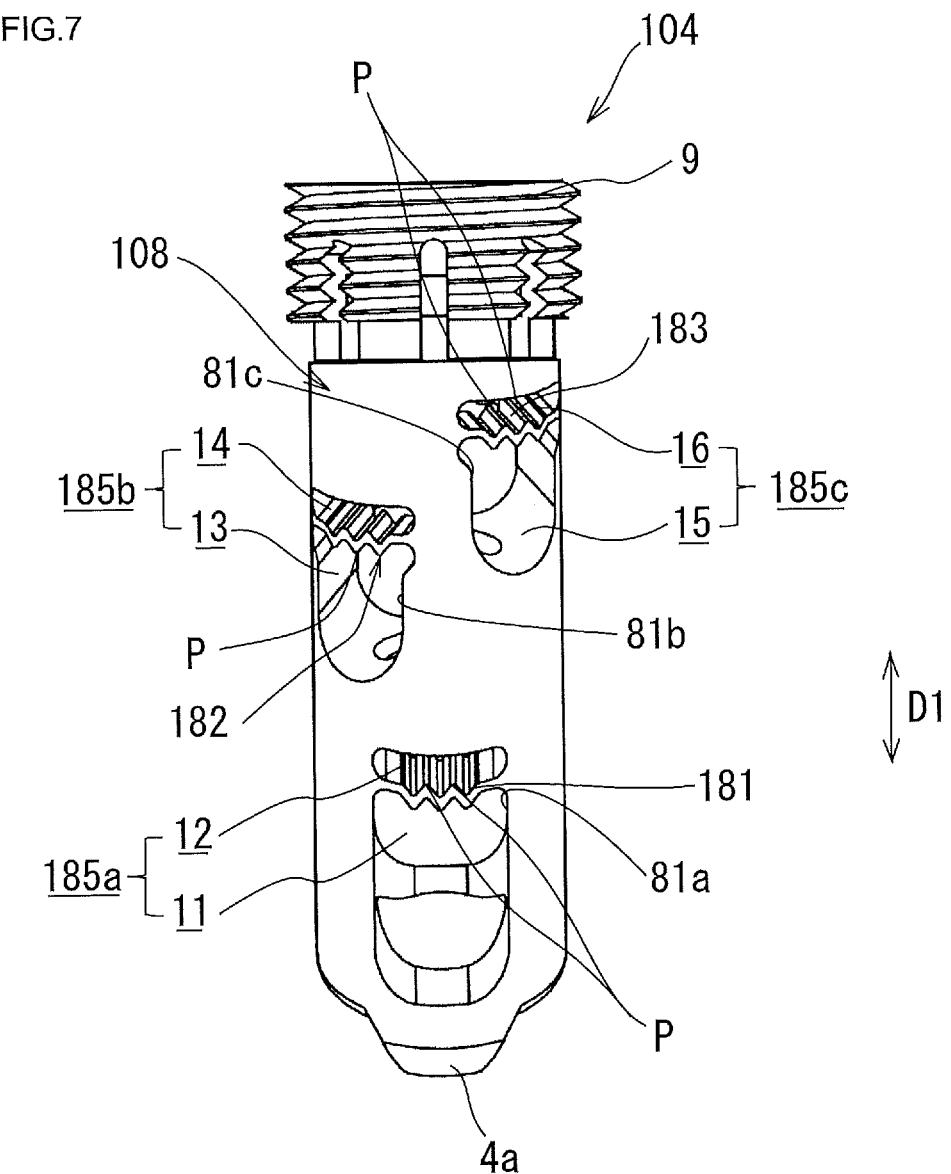

Next, a femur fixation apparatus according to a second embodiment of the invention will be described. With reference to FIGS. 6 and 7, a femur fixation apparatus 101 according to this embodiment is substantially the same as the femur fixation apparatus 1 described above, but differs in including an adjuster 104 instead of the adjuster 4. Thus, only the adjuster 104 will be described here, and explanation of the remainings will be omitted. Also, in this and following embodiments, parts and components that are substantially the same as those of the first embodiment are designated by the same reference numerals and description thereof will be omitted.

The adjuster 104 of this embodiment includes a sliding part 108 and the rotation part 9 rotatably connected to an upper end of the sliding part 108. The sliding part 108 is substantially the same as the sliding part 8, but the sliding part 108 is formed with interference prevention parts 185a, 185b, 185c instead of the interference prevention parts 85a, 85b, 85c, and the interference prevention parts 185a, 185b, 185c are divided by urging members 181, 182, 183 into main spaces 11, 13, 15 and subspaces 12, 14, 16, respectively. Each urging members 181, 182, 183 extends in a direction intersecting the up-down direction D1 and has both ends integrally connected to side walls of the interference prevention part 185a, 185b, 185c. That is, while the interference prevention parts 85a, 85b, 85c of the first embodiment have cantilevered structure, the interference prevention parts 185a, 185b, 185c of this embodiment have twin holding structure. Also, each interference prevention part 185a, 185b, 185c is in a waveform shape, and each crest part P of the waveform extends along an axial direction of the interference prevention part 185a, 185b, 185c (insertion direction of the anti-rotation pin 61 to 63/a direction along the axial direction X1, X2, X3 (FIG. 5)).

In this embodiment also, when the adjuster 104 is lowered with the anti-rotation pins 61 to 63 inserted through the auxiliary holes 3c to 3e (FIG. 1), then the anti-rotation pins 61, 62, 63 are pressed downward and fixed in place by the urging members 181, 182, 183, respectively, and thus the anti-rotation pins 61, 62, 63 are prevented from coming out the intramedullary nail 3. Also, having twin holding structure and the waveform shape, each interference prevention part 185a, 185b, 185c can further firmly fix the anti-rotation pin 61, 62, 63. It should be noted that examples of the waveform shape include a sine waveform shape, a triangular waveform shape, a square waveform shape, and a sawtooth waveform shape.

Third Embodiment

Figure 8:
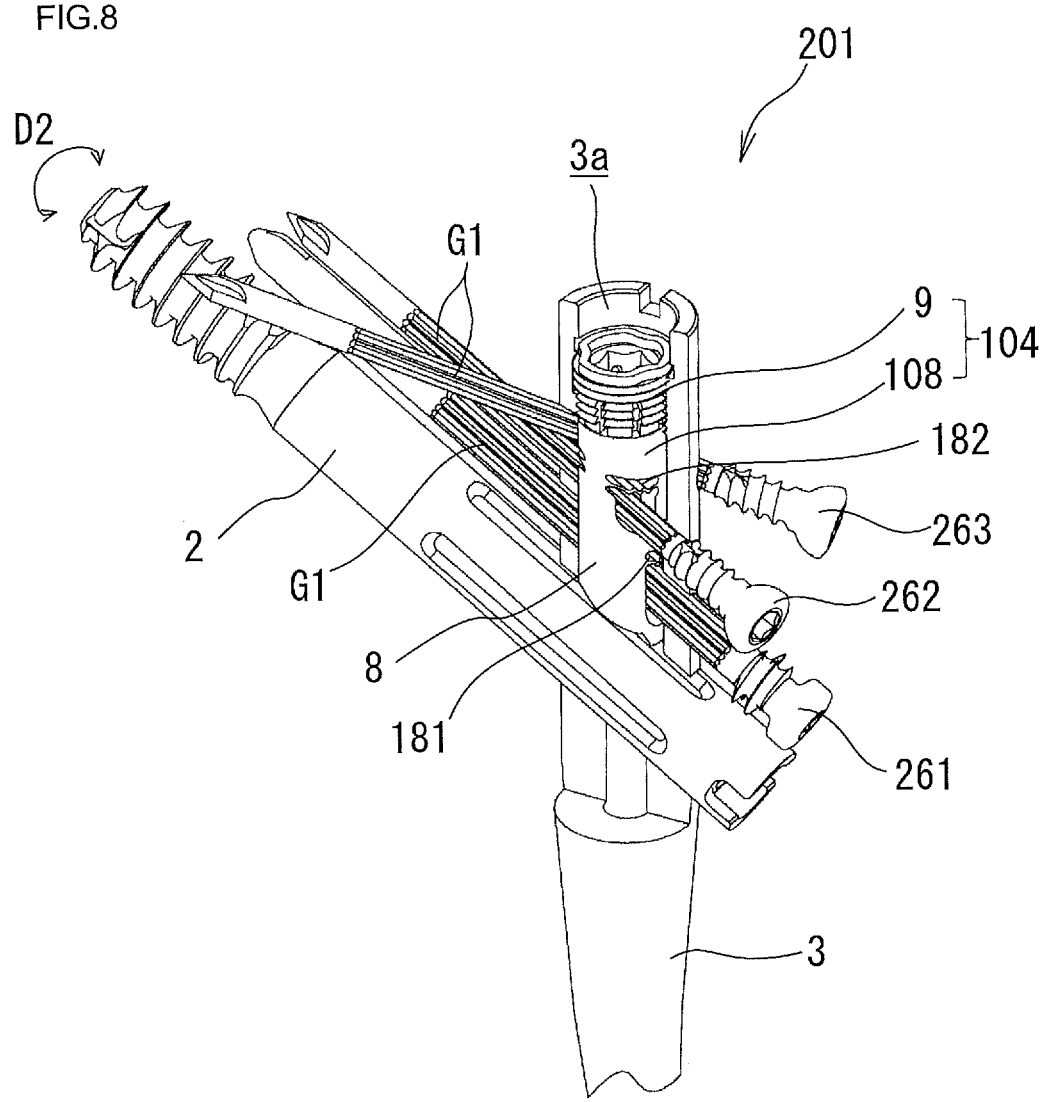
FIG. 8 A partial cross-sectional view of a femur fixation apparatus according to a third embodiment of the invention FIG. 9 A partial cross-sectional view of a femur fixation apparatus according to a fourth embodiment of the invention FIG. 10 Views of an adjuster of the femur fixation apparatus of FIG. 9, wherein (a) is a side view, (b) is a view as viewed from diagonally frontward, (c) is a front view, and (d) is perspective view FIG. 11 A partial cross-sectional view of a femur fixation apparatus according to a fifth embodiment of the invention FIG. 12($a$) is an exploded side view of a sliding part of an adjuster of the femur fixation apparatus of FIG. 11, (b) is a front view of a support part of the sliding part shown in FIG. (a), (c) is an exploded side view of the adjuster, (d) is a side view of the adjuster, (e) is a view of the adjuster as viewed from diagonally frontward, and (f) is a front view of the adjuster.

Next, a femur fixation apparatus according to a third embodiment of the invention will be described. With reference to FIG. 8, a femur fixation apparatus 201 according to this embodiment is substantially the same as the femur fixation apparatus 101 of the second embodiment, but differs in including anti-rotation pins 261, 262, 263 instead of the anti-rotation pins 61, 62, 63. Each anti-rotation pin 261, 262, 263 is formed with a plurality of grooves G1 extending in a longitudinal direction thereof.

Thus, when each anti-rotation pin 261, 262, 263 is pressed downward by each urging member 181, 182, 183 (FIG. 7) as described above, then the crest part P of each urging member 181, 182, 183 engages with the groove G1 of the anti-rotation pin 261, 262, 263. As a result, the anti-rotation pin 261, 262, 263 is further firmly fixed in place.

Fourth Embodiment

Figure 9:
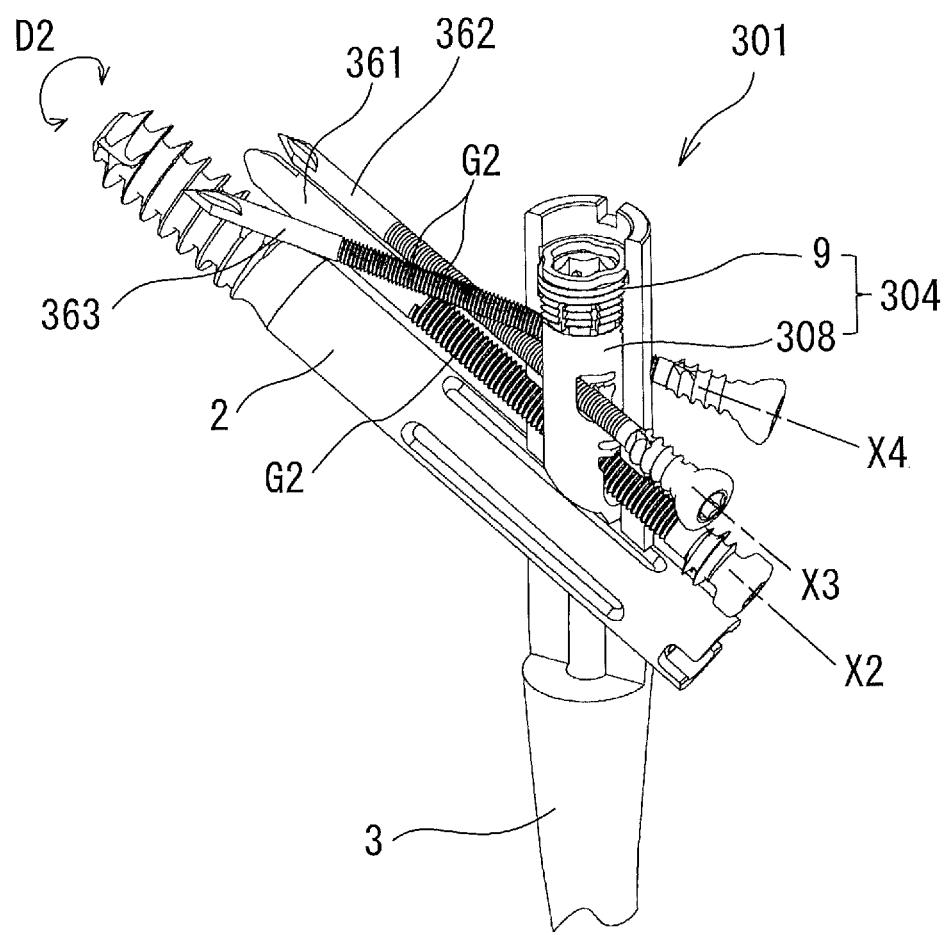
Figure 10:
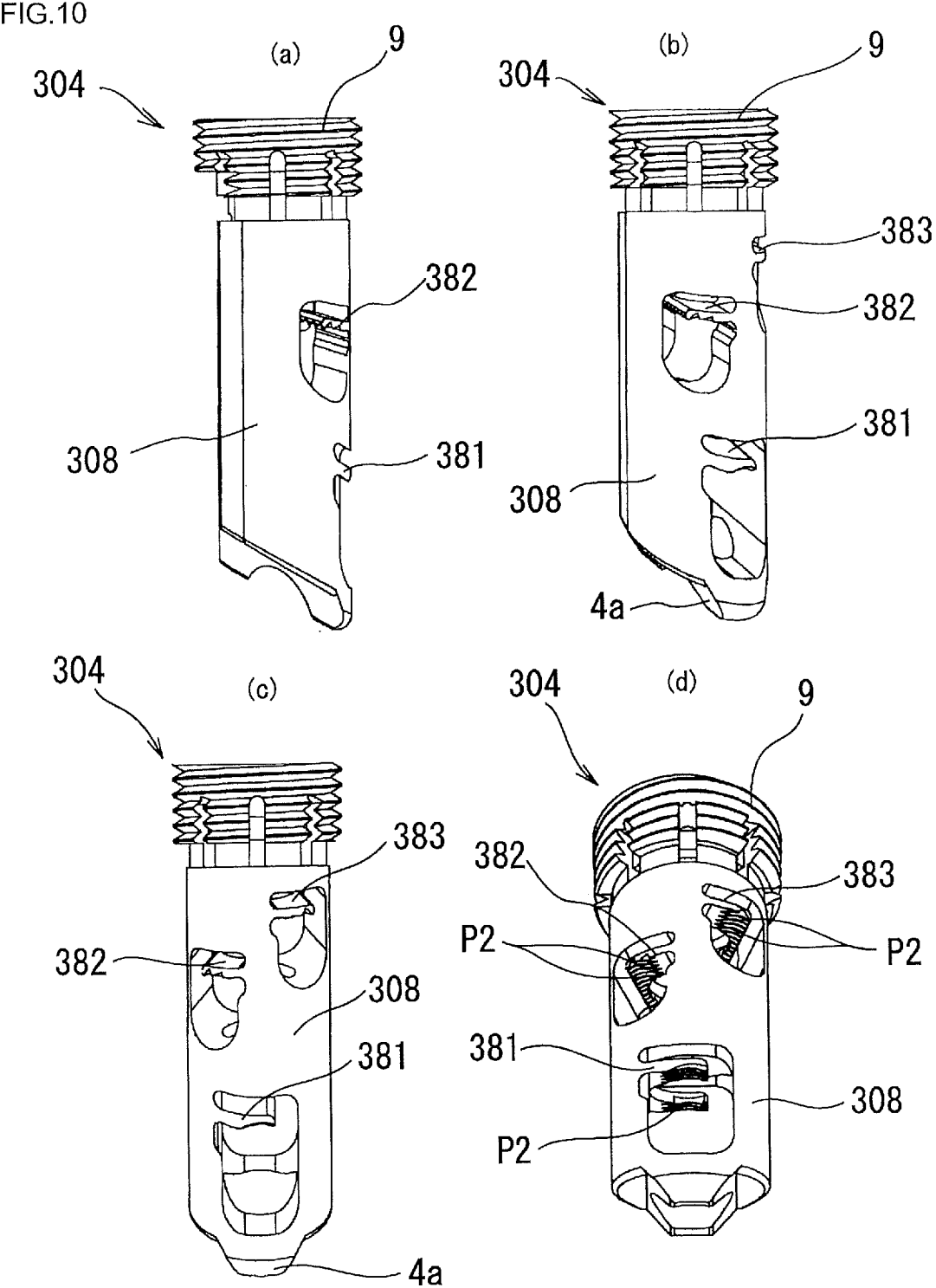

Next, a femur fixation apparatus according to a fourth embodiment of the invention will be described. With reference to FIGS. 9 and 10, a femur fixation apparatus 301 according to this embodiment is substantially the same as the femur fixation apparatus 1 of the first embodiment, but differs in including an adjuster 304 instead of the adjuster 4 and anti-rotation pins 361, 362, 363 instead of the anti-rotation pins 61, 62, 63.

The adjuster 304 includes a sliding part 308 and the rotation part 9 rotatably connected to an upper end of the sliding part 308. The sliding part 308 is substantially the same as the above-described sliding part 8, but differs from the sliding part 8 in that the sliding part 308 is formed with urging members 381, 382, 383 instead of the urging members 81, 82, 83. Although the urging members 381, 382, 383 are substantially the same as the urging members 81, 82, 83, lower surfaces thereof are formed with a plurality of protrusions P2 protruding downward. Each protrusion P2 extends in a direction along an extending direction of the urging member 381, 382, 383 (in a direction intersecting the insertion direction (axial direction X2, X3, X4) of the anti-rotation pin 361, 362, 363)). Each anti-rotation pin 361, 362, 363 has a peripheral surface formed with a groove G2 extending in its circumferential direction. Although the groove G2 in the example shown in FIG. 9 is a spiral groove, it may be a plurality of circular grooves aligned along the axial direction X2, X3, X4.

In this configuration, when each anti-rotation pin 361, 362, 363 is pressed downward by the urging member 381, 382, 383 in the same manner as in the first embodiment, then the protrusions P2 of each urging member 381, 382, 383 engage with the groove G2 of the anti-rotation pin 361, 362, 363. As a result, the anti-rotation pins 361, 362, 363 are firmly fixed in place. Also, because the protrusions P2 and the groove G2 extend in a direction intersecting the insertion direction of the anti-rotation pin 361, 362, 363 (axial direction X2, X3, X4), the anti-rotation pins 361, 362, 363 are more reliably prevented from coming out the intramedullary nail 3.

Fifth Embodiment

Figure 11:
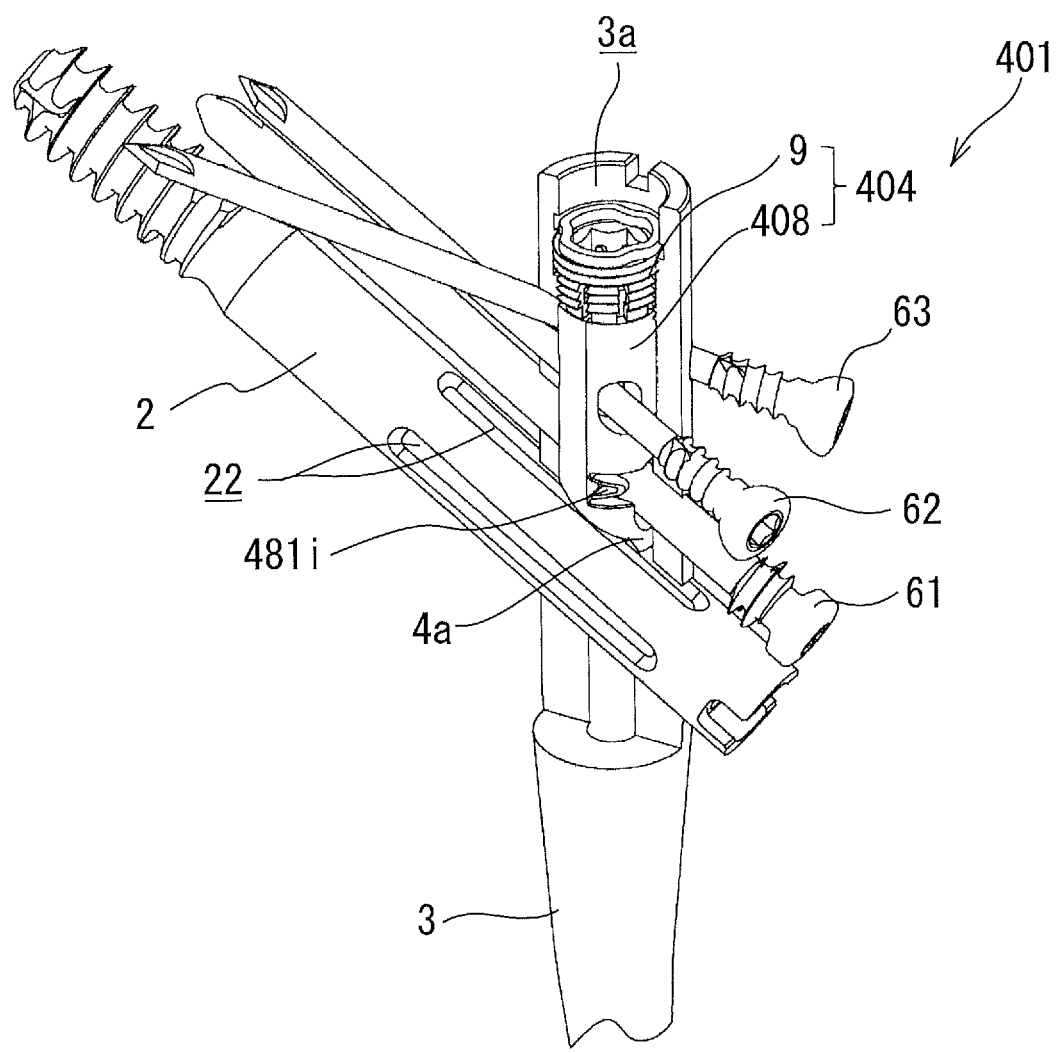
Figure 12:
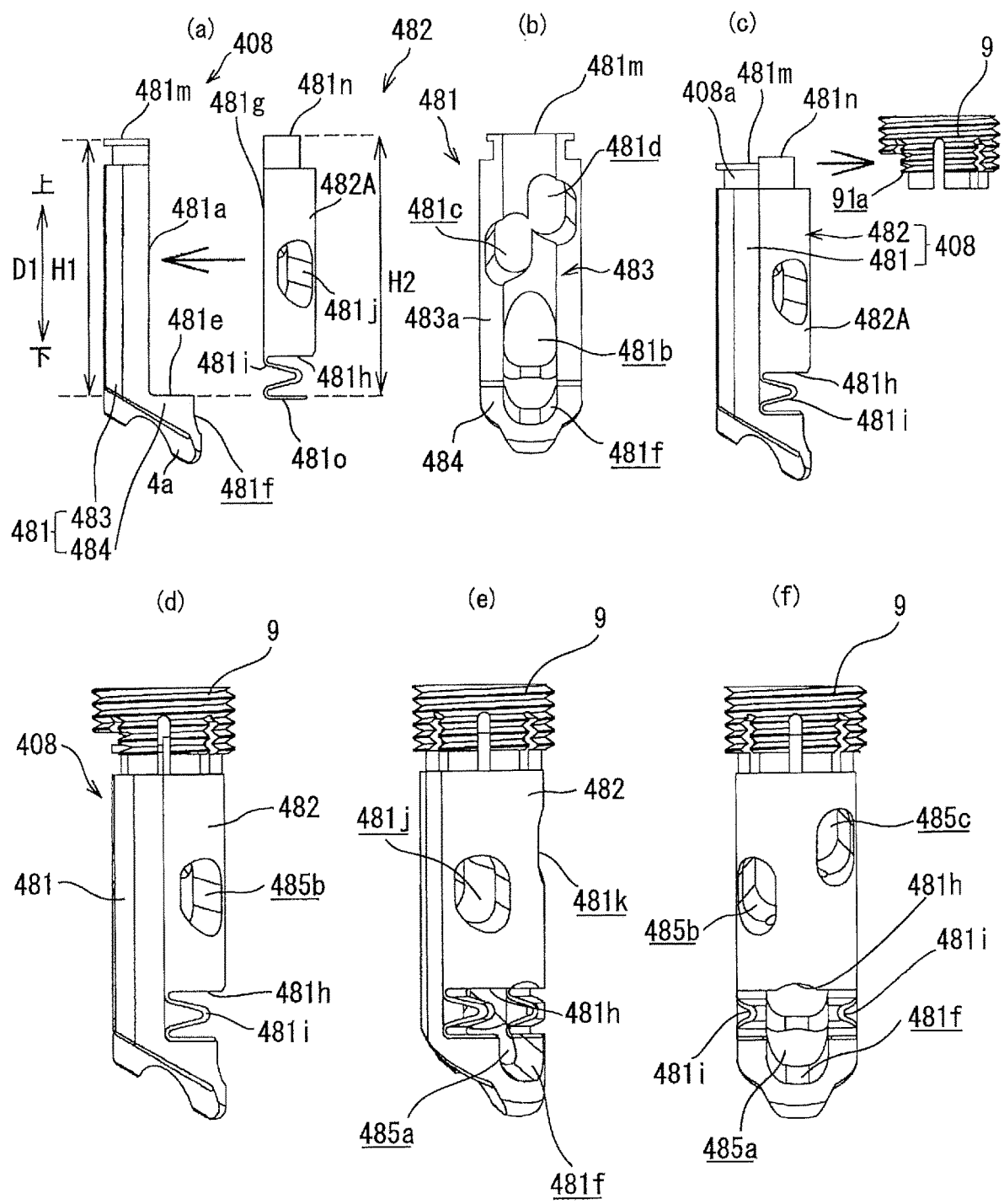
Figure 13:
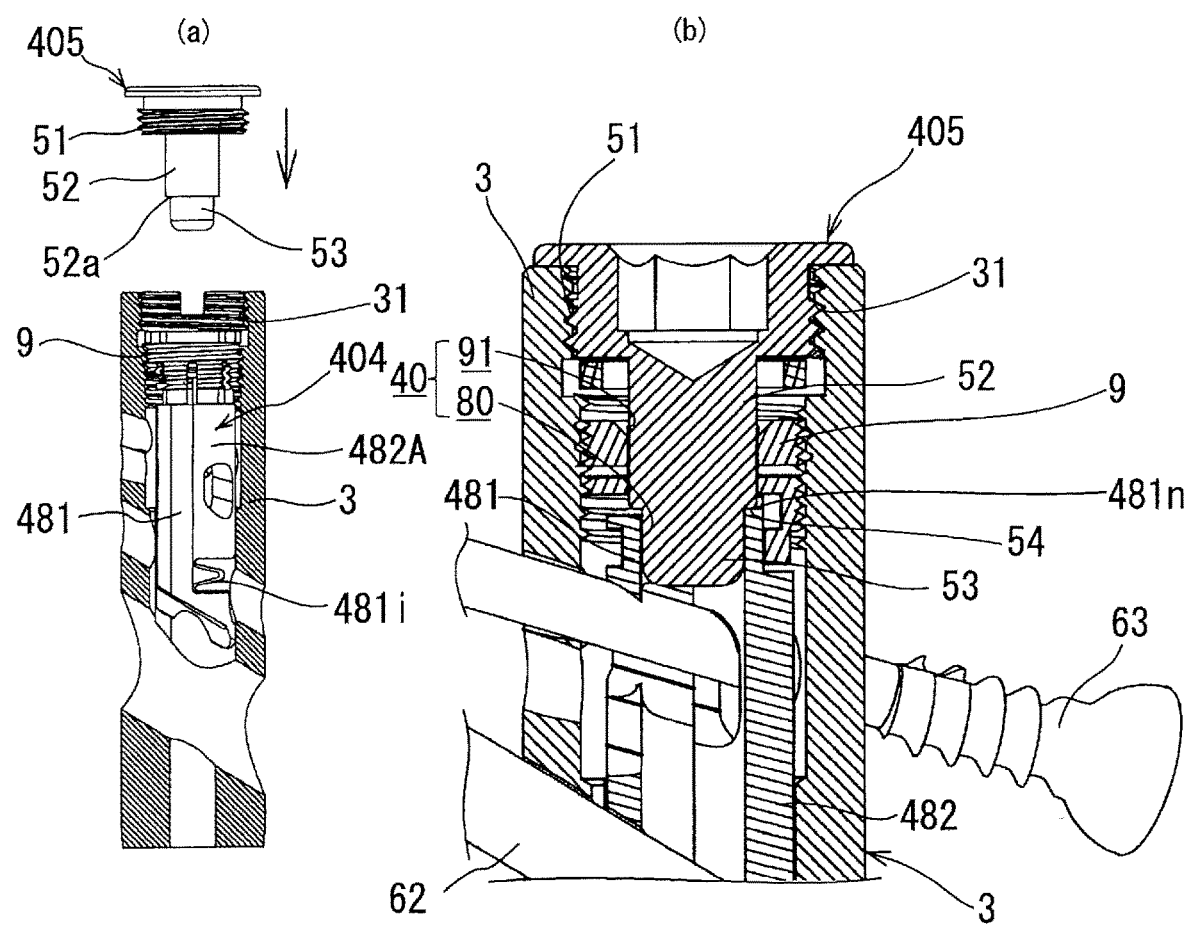
FIG. 13($a$) is a partial cross-sectional view of the femur fixation apparatus of FIG. 11, and (b) is an enlarged cross-sectional view of relevant parts of the femur fixation apparatus of FIG. 11.

Next, a femur fixation apparatus according to a fifth embodiment of the invention will be described. With reference to FIGS. 11 to 13, a femur fixation apparatus 401 according to this embodiment is substantially the same as the femur fixation apparatus 1 of the first embodiment, but differs in including an adjuster 404 instead of the adjuster 4 and an end cap 405 instead of the end cap 5.

The adjuster 404 includes a sliding part 408 and the rotation part 9 rotatably connected to an upper end 408*a* (FIG. 12(*c*)) of the sliding part 408. The sliding part 408 is formed with interference prevention parts 485*a*, 485*b*, 485*c* (FIG. 12(*f*)) instead of the interference prevention parts 85*a*, 85*b*, 85*c*. Also, the sliding part 408 is divided into a support part 481 and a movable part 482 (FIG. 12(*a*)).

As shown in FIG. 12(*a*), the support part 481 extends in the up-down direction D1 and has the stopper 4*a* at the bottom. The support part 481 has a first part 483 and a second part 484 formed integral with the first part 483. The first part 483 has a side surface 481*a* extending in the up-down direction D1. The side surface 481*a* is formed with spaces 481*b*, 481*c*, 481*d* (FIG. 12(*b*)). The second part 484 has a receiving surface 481*e* extending from the side surface 481*a* and facing upward. The receiving surface 481*e* is formed with a cutout 481*f* in a shape of a letter U.

As shown in FIGS. 12(*a*) and 12(*e*), the movable part 482 has a main part 482A and a pair of spring parts 481*i*, 481*i*. The main part 482A has a side surface 481*g* extending in the up-down direction D1 and a lower surface 481*h*. The side surface 481*g* is formed with spaces 481*j*, 481*k*. The pair of spring parts 481*i*, 481*i* extends downward from the lower surface 481*h* of the main part 482A and is leaf springs in a shape of a waveform.

The adjuster 404 having this configuration is assembled in the following manner. First, with reference to FIG. 12(*a*), the side surface 481*g* of the movable part 482 is brought into confrontation with the side surface 481*a* of the support part 481, and the pair of spring parts 481*i*, 481*i* is placed on the receiving surface 481*e* of the support part 481 to assemble the sliding part 408 as shown in FIG. 12(*c*). Then, the upper end 408*a* of the sliding part 408 is inserted into the rotation part 9 through a cutout 91*a* of the rotation part 9.

In this condition, the space 481*b* of the support part 481 and the cutout 481*f* function as the interference prevention part 485*a*, and the space (first space) 481*c* of the support part 481 and the space (second space) 481*j* of the movable part 482 function as the interference prevention part 485*b*, and the space (third space) 481*d* of the support part 481 and the space (fourth space) 481*k* of the movable part 482 function as the interference prevention part 485*c*.

Here, in a free-state shown in FIG. 12(*c*), an upper end 481*n* of the movable part 482 is positioned higher than an upper end 481*m* of the support part 481. That is, as shown in FIG. 12(*a*), a distance H2 from the upper end 481*n* of the movable part 482 to a lower end 481 of the movable part 482 is set greater than a distance H1 from the upper end 481*m* of the support part 481 to the receiving surface 481*e*. When the upper end 481*n* of the movable part 482 is pressed downward from this state, then the pair of spring parts 481*i*, 481*i* is compressed in the up-down direction D1, and thus the spaces 481*j*, 481*k* of the movable part 482 are lowered relative to the support part 481.

As shown in FIG. 13(*a*), the end cap 405 has a male screw part 51 for threadedly engaging with the female screw part 31 of the intramedullary nail 3, a body 52 extending downward from the male screw part 51, and a protrusion 53 extending downward from a lower surface of the body 52 and having a smaller diameter than the body 52. A lower surface of the body 52 functions as a pressing surface 52*a*. As shown in FIG. 13(*b*), the through hole 40 of the adjuster 404 has the operation hole 91 formed in the rotation part 9 and a through hole 80 formed in the sliding part 408 in fluid communication with the operation hole 91. The body 52 is configured to be insertable into the operation hole 91 of the rotation part 9, and the protrusion 53 is configured to be insertable into the through hole 80 of the sliding part 408.

The femur fixation apparatus 401 having the above configuration is fitted to a femur as described next. First, the intramedullary nail 3 with the adjuster 404 preset therein is inserted into marrow of the femoral shaft T1 (FIG. 5) to a predetermined depth, and the lag screw 2 and the anti-rotation pins 61 to 63 are inserted through the intramedullary nail 3 and the adjuster 404 into the femur (T) as in the first embodiment.

In this condition, the rotation part 9 of the adjuster 404 is rotated in a predetermined direction with the external operation tool. As a result, the entire adjuster 404 is lowered. The stopper 4a is engaged with the groove 22 to prevent the rotation of the lag screw 2, entering the lag screw 2 into the above-described slidable state or the completely locked state. Afterward, when the end cap 405 is inserted into the long hole 3a of the intramedullary nail 3, then the pressing surface 52a of the end cap 405 abuts the upper end 481n of the movable part 482 of the adjuster 404. When the male screw part 51 of the end cap 405 is threadedly engaged with the female screw part 31 of the intramedullary nail 3 in this state, the pressing surface 52a of the end cap 405 presses the movable part 482 downward to compress the spring parts 481i, 481i, lowering the main part 482A of the movable part 482 relative to the support part 481. The anti-rotation pin (another anti-rotation member) 61 is pressed downward and fixed in place by the lower surface 481h of the main part 482A, and the anti-rotation pins 62, 63 are pressed downward and fixed in place by upper walls of the spaces 481j, 481k. In this manner, the anti-rotation pins 61, 62, 63 are prevented from coming out the intramedullary nail 3.

As described above, according to the femur fixation apparatus 401 of this embodiment, while the height position of the entire adjuster 404 (that is, pressing force of the adjuster 404 onto the lag screw 2) is adjusted by a rotation amount of the rotation part 9, the height position of the movable part 482 relative to the support part 481 (that is, pressing force of the movable part 482 onto the anti-rotation pins 61, 62, 63) is adjusted by a fastening amount of the end cap 405. Thus, it is possible to adjust the pressing force (fixing force) to the lag screw 2 and the pressing force (fixing force) to the anti-rotation pins 61, 62, 63 separately, making it easier to adjust the pressing force. Also, in this embodiment, the end cap 405 directly presses the anti-rotation pins 61, 62, 63 without using urging force of an urging member, pressing force against the anti-rotation pins 61, 62, 63 is enhanced.

It should be noted that the lower surface 481h of the main part 482A may be formed with a recess as shown in FIG. 12(e) or a protrusion, or formed flat without a recess or a protrusion.

While the femur fixation apparatuses according to the embodiments of the invention have been described with reference to the drawings, the invention is not limited to these embodiments, but various changes and modifications may be made therein without departing from the spirit of the invention.

For example, in the above-described fifth embodiment, the sliding part 408 of the adjuster 404 is divided into the support part 481 and the movable part 482. However, in a different embodiment, the support part 481 and the movable part 482 (more specifically, the receiving surface 481e of the support part 481 and lower ends of the spring parts 481i, 481i) are preferably formed integrally with each other.

Also, although the adjuster 404 includes the pair of spring parts 481i, 481i in the above fifth embodiment, the adjuster preferably includes a single spring in a different embodiment, and the adjuster can include at least one spring.

Further, in a different embodiment, it is preferable that the interference prevention parts 485a, 485b, 485c shown in FIG. 12(f) be provided with the urging members 81, 82, 83 shown in FIG. 4(d), the urging members 181, 182, 183 shown in FIG. 7, or the urging members 381, 382, 383 shown in FIG. 10(c). In this case, the lower surface 481h of the movable part 482 is formed with a cutout, and the urging member is formed at the height position of the lower surface 481h shown in FIG. 12(f). Also, the spaces 481j, 481k of the movable part 482 are expanded upward, and the urging members are formed at the height positions of the upper surfaces of the interference prevention parts 485b, 485c shown in FIG. 12(f).

EXPLANATION OF REFERENCE NUMBERS 1, 101, 201, 301, 401 femur fixation apparatus
2 lag screw
3 intramedullary nail
4, 104, 304, 404 adjuster
4a stopper
5, 405 end cap (cover member)
8, 108, 308, 408 sliding part
9 rotation part
61, 62, 63, 261, 262, 263, 361, 362, 363, anti-rotation pin (anti-rotation member)
481 support part
481i spring part
482 movable part
482A main part 482
D1 first direction (up-down direction)

The invention claimed is:

1. A femur fixation apparatus comprising:
an intramedullary nail extending in a first direction;
a first anti-rotation member configured to be inserted through the intramedullary nail; and
an adjuster fitted in the intramedullary nail, wherein:
the adjuster includes a rotation part and a sliding part extending in the first direction;
the sliding part is unrotatable and slide-movable in the first direction relative to the intramedullary nail and has a first end on a first side in the first direction and a second end on a second side opposite to the first side in the first direction;
the rotation part is rotatably and threadedly engaged in the intramedullary nail and rotatably connected to the first end of the sliding part;
the sliding part is formed with a first space through which the first anti-rotation member is inserted;
the sliding part has a first urging member extending from a side wall of the first space into the first space; and
when the rotation part is rotated in a predetermined direction relative to the intramedullary nail, then the adjuster moves toward the second side relative to the intramedullary nail, and the first urging member presses toward the second side and fixes in place the first anti-rotation member.

2. The femur fixation apparatus according to claim 1, further comprising a second anti-rotation member configured to be inserted through the intramedullary nail, wherein:
the sliding part is formed with a second space through which the second anti-rotation member is inserted;
the sliding part has a second urging member extending from a side wall of the second space into the second space;
when the adjuster moves toward the second side relative to the intramedullary nail, then the second urging member presses toward the second side and fixes in place the second anti-rotation member; and the first space and the second space are at least partially aligned with each other in a second direction perpendicular to the first direction.

3. The femur fixation apparatus according to claim 1 or 2, claim 1, wherein:
the first urging member partitions the first space into a main space and a subspace;
the main space is configured to be inserted with the first anti-rotation member; and
the first urging member has a waveform shape.

4. The femur fixation apparatus according to claim 1, wherein:
the first urging member is formed with a protrusion extending toward the second side;
the first anti-rotation member has a peripheral surface formed with a groove; and
when the adjuster moves toward the second side relative to the intramedullary nail, then the protrusion of the first urging member engages with the groove of the first anti-rotation member.

5. The femur fixation apparatus according to claim 3, wherein:
the first urging member is formed with a protrusion extending toward the second side;
the first anti-rotation member has a peripheral surface formed with a groove; and
when the adjuster moves toward the second side relative to the intramedullary nail, then the protrusion of the first urging member engages with the groove of the first anti-rotation member.

6. A femur fixation apparatus comprising:
an intramedullary nail extending in a first direction;
a lag screw configured to be inserted through the intramedullary nail;
an anti-rotation member configured to be inserted through the intramedullary nail; and
an adjuster fitted in the intramedullary nail, wherein:
the adjuster includes a rotation part and a sliding part extending in the first direction;
the sliding part is unrotatable and slide-movable in the first direction relative to the intramedullary nail and has a first end on a first side in the first direction and a second end on a second side opposite to the first side in the first direction;
the rotation part is rotatably and threadedly engaged in the intramedullary nail and rotatably connected to the first end of the sliding part;

the sliding part has a support part and a movable part movable in the first direction relative to the support part;
the movable part has a main part and a spring part, the main part having a first end on the first side and a second end on the second side, the spring part extending from the second end of the main part toward the second side, the spring part being deformable in the first direction;
the support part and the main part of the movable part are respectively formed with a first space and a second space through which the anti-rotation member is inserted; and
when the movable part is pressed toward the second side, then the spring part is compressed, and the main part moves relative to the support part toward the second side, thereby fixing in place the anti-rotation member inserted through the first space and the second space.

7. The femur fixation apparatus according to claim 6, further comprising an end cap that threadedly engages with the intramedullary nail, wherein:
the end cap has a pressing surface;
the support part has an end on the first side, and the first end of the main part is located toward the first side than the end of the support part; and
when the end cap is threadedly engaged with the intramedullary nail, then the pressing surface of the end cap abuts the first end of the main part of the movable part and presses the movable part toward the second side.

8. The femur fixation apparatus according to claim 6, wherein:
the lag screw is formed with a groove;
the second end of the sliding part is formed with a stopper for engaging with the groove of the lag screw; and
the spring part is located between the stopper and the second space in the first direction.

9. The femur fixation apparatus according to claim 6, further comprising another anti-rotation member configured to be inserted through the intramedullary nail, wherein:
the main part of the movable part is located toward the first side than the another anti-rotation member inserted through the intramedullary nail; and
when the main part moves toward the second side relative to the support part, then the second end of the main part abuts and presses the another anti-rotation member toward the second side.

* * * * *